(12) United States Patent
Buelna et al.

(10) Patent No.: US 7,566,429 B2
(45) Date of Patent: Jul. 28, 2009

(54) CATALYTIC REACTIVE SEPARATION SYSTEM FOR ENERGY-EFFICIENT PRODUCTION OF CUMENE

(75) Inventors: Genoveva Buelna, Nuevo Laredo (MX); Tina M. Nenoff, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 540 days.

(21) Appl. No.: 11/152,997

(22) Filed: Jun. 14, 2005

(65) Prior Publication Data

US 2006/0281958 A1 Dec. 14, 2006

(51) Int. Cl.
*B01J 8/02* (2006.01)
*C07C 2/66* (2006.01)

(52) U.S. Cl. .............. 422/211; 422/198; 422/202; 422/234; 585/446; 585/447; 585/467; 203/DIG. 6

(58) Field of Classification Search .................. None
See application file for complete search history.

(56) References Cited

U.S. PATENT DOCUMENTS

| | | | | |
|---|---|---|---|---|
| 2,081,322 | A * | 5/1937 | Carney | 570/252 |
| 2,555,606 | A * | 6/1951 | Potts | 530/222 |
| 3,907,709 | A * | 9/1975 | List et al. | 502/8 |
| 4,849,569 | A | 7/1989 | Smith, Jr. | |
| 4,891,458 | A * | 1/1990 | Innes et al. | 585/323 |
| 5,019,669 | A | 5/1991 | Adams et al. | |
| 5,055,627 | A | 10/1991 | Smith, Jr. et al. | |
| 5,120,403 | A | 6/1992 | Smith, Jr. | |
| 5,204,064 | A | 4/1993 | Smith, Jr. | |
| 5,221,441 | A | 6/1993 | Smith, Jr. | |
| 5,243,115 | A | 9/1993 | Smith, Jr. et al. | |
| 5,262,576 | A | 11/1993 | Smith, Jr. | |
| 5,877,384 | A | 3/1999 | Gimpel et al. | |
| 6,315,964 | B1 * | 11/2001 | Knifton et al. | 422/190 |
| 6,504,071 | B2 * | 1/2003 | Zhang et al. | 585/467 |

(Continued)

FOREIGN PATENT DOCUMENTS

JP  62087549 A  *  4/1987

OTHER PUBLICATIONS

Du et al. Study on alkylation of benzene with ethylene over beta-zeolite catalyst to ethylbenzene by in situ IR. Journal of Molecular Catalysis A: Chemical 197 (2002) 253-261.*

(Continued)

*Primary Examiner*—Jennifer A Leung
(74) *Attorney, Agent, or Firm*—Robert D. Watson

(57) ABSTRACT

The present invention relates to an atmospheric pressure, reactive separation column packed with a solid acid zeolite catalyst for producing cumene from the reaction of benzene with propylene. Use of this un-pressurized column, where simultaneous reaction and partial separation occur during cumene production, allow separation of un-reacted, excess benzene from other products as they form. This high-yielding, energy-efficient system allows for one-step processing of cumene, with reduced need for product purification. Reacting propylene and benzene in the presence of beta zeolite catalysts generated a selectivity greater than 85% for catalytic separation reactions at a reaction temperature of 115 degrees C and at ambient pressure. Simultaneously, up to 76% of un-reacted benzene was separated from the product; which could be recycled back to the reactor for re-use.

19 Claims, 5 Drawing Sheets

U.S. PATENT DOCUMENTS 6,642,425 B2 11/2003 Winder et al.
2003/0171630 A1 9/2003 Winder et al.

OTHER PUBLICATIONS

S. Siffert, L. Gaillard & B. L. Su, Alkylation of Benzene by Propene on a Series of Beta Zeolites: Toward . . . , Journ. of Molecular Catalysis A: Chemical 153 (2000) 267-279.

A. Corma, V. Martinez-Soria, E. Schnoeveld, Alkylation of Benzene with Short-Chain . . . , Jornal of Catalysis 192, 163-173 (2000).

J. D. Shoemaker, E. M. Jones, Jr., Cumene by Catalytic Distillation, Hydrocarbon Processing Jun. 1987.

A. Tuchlenski, et al, Reactive Distillation—Industirl Applications, Process Design & Scale-up, Chemical Engineering Science 56 (2001) 387-394.

Tamara Hartenberger, Maximizing Energy Efficiency in the Production of Cumene, Sandia National Labs Student Symposium, Albuquerque, NM, Aug. 5, 2003.

Genoveva Buelna, Modified Beta Zeolites for Alkylation of Benzene Using Batch and Continuous Fixed-bed Reactors, 18th North American Catalysis Society Meeting, Jun. 1-6, 2003.

June, et al, Alkylation of Benzene with Propene Over H Zeolite, Chemical Research in Chinese Universities, vol. 11, No. 1 (1995).

Hongfei Lin, et al, Study on a Catalytic Distillation column with a Novel Internal, Chem. Eng. Comm., 189: 1498-1516, 2000.

John F. Knifton, et al, A New, Improved, Solid-Acid Catalyzed process for Generating Linear Alkylbenzenes (LABs), Catalysis Letters vol. 75, No. 1-2, 2001.

C. Noeres et al, Reactive Distillation: Non-Ideal Flow Behaviour of the Liquid Phase in Structured Catalytic Packings, Chemical Eng. Science 57 (2002) 1545-1549.

Achim Hoffman, et al, Scale-Up of Reactive Distillation Columns with Catalytic Packings, Chemic Eng and Processing 4r3 (2004) 383-395.

K. R. Westerter, Maltifunctional Reactors, Chemical Eng. Science, vol. 47, No. 9-11, pp. 2195-2206, 1992.

Shubham P. Chopade, et al, Acetelization of Glycol with Formaldehyde Using Cation-Exchange Resins as Catalysts . . . , Reactive & Functional Polymers 34 (1997) 37-45.

L. A. Smith, New MTBE Design Now Commercial, Hydrocarbon Processing, Mar. 1982, pp. 121-124.

W. Li, et al, Effect of Reactor Type on the Activity Obtained During the Hydration of Propylene over Zeolite Beta Catalysts, 12th International Zeolite Conf, 1999 Materials Research Society, pp. 1313-1317.

* cited by examiner

CATALYTIC REACTIVE SEPARATION SYSTEM FOR ENERGY-EFFICIENT PRODUCTION OF CUMENE

FEDERALLY SPONSORED RESEARCH

The United States Government has rights in this invention pursuant to Department of Energy Contract No. DE-AC04-94AL85000 with Sandia Corporation.

CROSS-REFERENCE TO RELATED APPLICATIONS

None

BACKGROUND OF THE INVENTION

Cumene (isopropylbenzene) is an important feedstock chemical for the production of phenol, acetone, and alpha-methyl styrene. It is also used as an important raw material in the manufacture of pesticide intermediates such as p-cumidine, and finds application in the manufacture of cumene hydroperoxide and dicumyl peroxide, which are used as initiators in polymerization processes, such as grafting vinyl monomers onto polymer backbones, curing of resins and rubbers and the like. Further, it is used as a raw material in the production of acetophenone and diisoproplyl benzene; as a solvent for flats and resins; as a thinner for paints, enamels, and lacquers; and as a component in aviation gasolines.

Current technologies for production of cumene require use of large excess amounts of reactant benzene. Benzene is an expensive and carcinogenic organic reactant, therefore it is desirable to use either the least amount of benzene possible, or preferably, utilize a cheaper, less dangerous chemical than benzene. The technologies currently in use further require an energy-intensive, 2-step distillation process, requiring excess reactants and a necessary cooling time between the two steps.

Hydrocarbon production usually relies upon the catalytically driven chemical reaction between reactants and products, followed by energy-intensive distillation purification steps. Such separation by distillation is based on the differences in boiling points and volatilities of the individual components. When heat is applied, the vapor of a boiling mixture will be richer in the components having lower boiling points. Thus, when the vapor is cooled and condensed, the condensate contains more of the volatile components. Simultaneously, the primary mixture will contain more of the components that are less volatile. Recent technologies, such as catalytic distillation and reactive distillation, achieve catalytic reaction and continuous separation of unreacted reactant and products by distillation in one step, in a single catalytic distillation reactor column. The advantage of using a solid-catalyzed reaction, over a catalyst that acts as distillation packing inside the distillation column, is more pronounced when used in reactions limited by equilibrium. While these systems still require that reaction by-products be separated from the cumene, they now contain an energy-efficient distillation or fractionating step for separating unreacted benzene from the products.

However, these later technologies require the use of high pressures in the column to operate, given the fact that for distillation to take place at least part of the reacting mixture has to be in liquid phase. For reactor design that have a reaction temperature inherently limited by the boiling point of the liquid composition of the reacting components, then the use of higher column pressures increases the boiling temperature, which can be used to increase the yield of the reaction products by allowing the reactor to operate at a higher reaction temperature. However, if the column pressure is fixed in this type of design, then adding additional heat to the liquid composition only increases the amount of vapor being generated by boiling; rather than increasing the reactant's temperature.

It would be desirable and beneficial to utilize a production process that does not require high pressure (which requires specialized equipment and excess use of energy), and which utilizes only one separation column at atmospheric pressure, for reduction of cost, time, energy, and potential safety hazards.

Against this background, the present invention was developed.

SUMMARY OF THE INVENTION

The present invention relates to an atmospheric pressure, reactive separation column packed with a solid acid zeolite catalyst for producing cumene from the reaction of benzene with propylene. Use of this non-pressurized column, where simultaneous reaction and partial separation occur during cumene production, allow separation of un-reacted, excess benzene from other products as they form. This high-yielding, energy-efficient system allows for one-step processing of cumene, with reduced need for product purification. Reacting propylene and benzene in the presence of beta zeolite catalysts generated a selectivity greater than 85% for catalytic separation reactions at a reaction temperature of 115 degrees C. and at ambient pressure. Simultaneously, up to 76% of un-reacted benzene was separated from the product; which could be recycled back to the reactor for re-use.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

Figure 1:
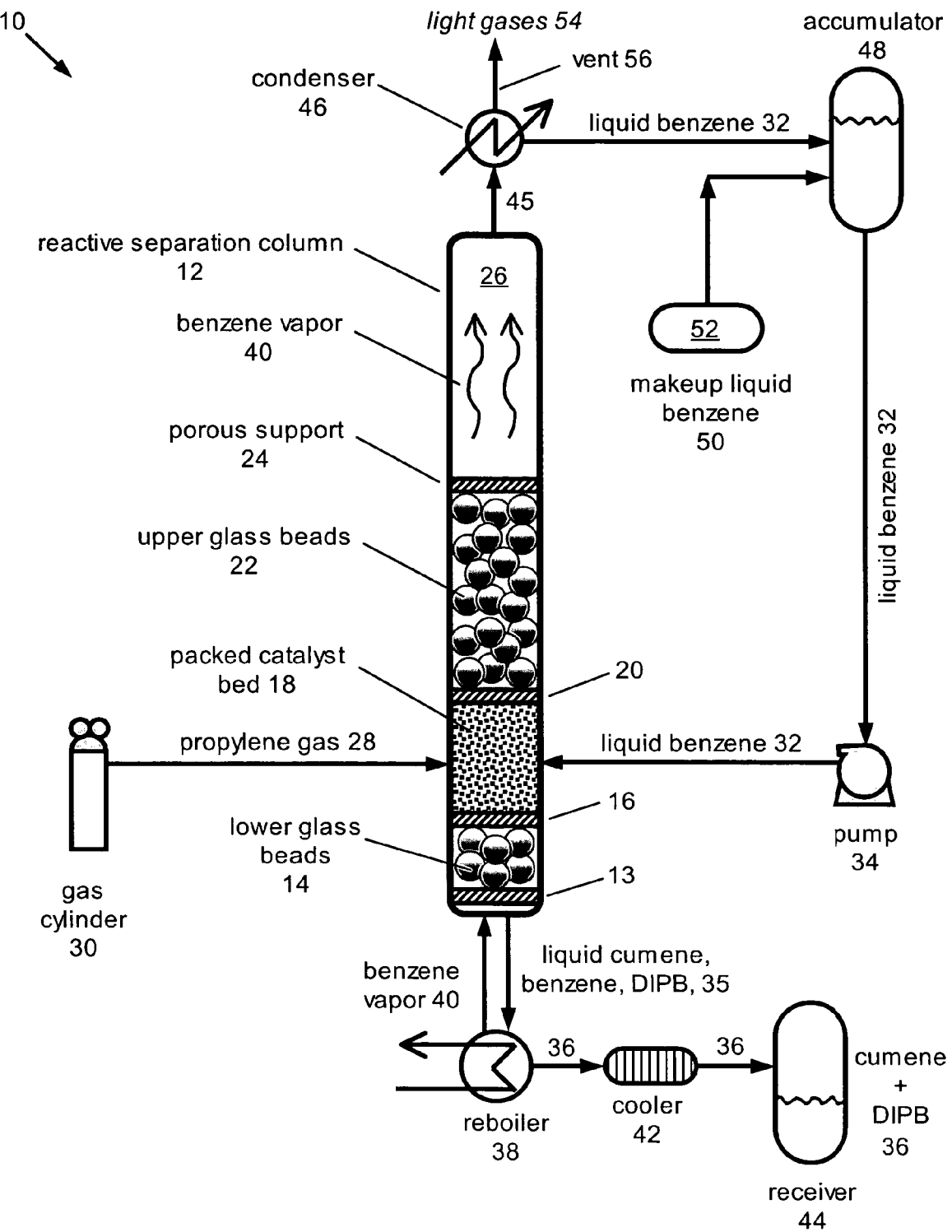
FIG. 1 shows a first example of a schematic process flow chart for producing cumene, including a schematic cross-section view of a reactive separation column, according to the present invention.

FIG. 1 shows a schematic process flow chart of a system 10 for producing cumene, including a schematic cross-section view of a reactive separation column 12, according to the present invention. The catalytic reaction separation system 10 comprises: vertically-oriented reactive separation column 12; with associated plumbing, pumps and other equipment for a) feeding the reactants (propylene gas 28 and liquid benzene 32) into catalyst bed 18; b) separating crude alkylation products (cumene+DIPB 36); c) for recycling un-reacted excess benzene 32 back to reactor 12; and d) feeding liquid benzene 50 into system 10. Since column 12 is not pressurized and operates at ambient (atmospheric) pressure, then it's design and construction is not required to satisfy typical pressure vessel design requirements (e.g., ASME Pressure Vessel Code), which reduces the system's cost and increases the operational safety.

Reactive separation column 12 comprises the following structures, listed from bottom to top: first porous support 13, lower glass beads 14, second porous support 16, packed catalyst bed 18, third porous support 20, upper glass beads 22, fourth porous support 24, and open volume 26. Propylene gas 28 (which can be mixed with nitrogen gas), is supplied from gas cylinder 30 and fed into the middle of catalyst bed 18. The other reactant, liquid benzene 32, is fed into the middle of catalyst bed 18 on the opposite side. Column 18 may be controllably-heated (or cooled) to an elevated temperature (e.g., 115 degrees C) by external (or internal) heating (or cooling) means (not shown), such as an external electric resistance heating jacket, or, by circulation of a hot fluid or gas in pipes or tubes wrapped around the outside of column 12 (with appropriate thermal insulation, temperature sensors, etc.). Alternatively, internal heating (or cooling) means (e.g., internal electric heating elements or internal coils carrying heating/cooling fluids) may be used to directly heat the catalyst bed 18, rather than trying to heat the exterior structural wall of column 12.

In one embodiment, the entire vertical height of column 12 may be externally heated to a uniform temperature (e.g., 115 degrees C). In another embodiment, only the packed catalyst bed 18 is externally heated. The entire vertical extent of column 12 may be thermally insulated. Since the reaction of propylene and benzene to produce cumene is exothermic, catalytic bed 18 will generate its own heat during operation, thereby reducing the amount of external heat that needs to be applied to the column (or inside the column) during operation.

Since the reactive separation column 12 is vented to the ambient environment outside, it cannot be pressurized above the surrounding ambient pressure. Hence, the temperature of catalyst bed 18 cannot be controlled by changing the column's internal pressure. Instead, it is controlled by externally increasing the bed temperature. This is different from some boiling reactive separation columns, which—because the liquid reactants' boiling point increases with increased pressure—increase the internal bed temperature by increasing the column's internal pressure.

The temperature of catalyst bed 18 may be controlled, by adjusting the external heating means described above, to be in the range from about 80 degrees C to 150 degrees C, which corresponds to the boiling temperature of benzene (80 degrees C) and cumene (150 degrees C), respectively, at atmospheric pressure. Preferably, the temperature of catalyst bed 18 is about 115 C (which is halfway in-between 80 degrees C and 150 degrees C). At 115 C, most of the liquid benzene 32 reactant that is injected into catalyst bed 18 quickly flashes into benzene vapor 40 because the bed's temperature exceeds the boiling point of benzene (80 degrees C) at ambient pressure. The vaporized benzene 40 rises through the catalyst bed 18, upper glass beads 22, and open volume 26, to the top of column 12, where it exits through pipe 45. However, any injected liquid benzene 32 that does not vaporize inside bed 18 falls down under gravity through lower glass beads 14, and exits through the bottom of column 12 into reboiler 38.

The other reactant, propylene gas 28 (which can be preheated to, e.g., the temperature of the catalyst bed 18, if needed, before injection into column 12), is injected into the middle of catalyst bed 18, then permeates through bed 18, where it mixes and reacts with the rising benzene vapor 40 in the presence of the inherently large surface area of packed catalyst particles (e.g., beta zeolite powder) to produce liquid cumene 36 (and minor, heavy byproducts, such as DIPB). Since the temperature of catalyst bed 18 (e.g., 115 degrees C) is greater than the boiling point of cumene (152 degrees C at atmospheric pressure), then it follows that the synthesized cumene 36 is primarily in the liquid state. Liquid cumene 36 flows down under gravity through catalyst bed 18, through lower glass beads 14, and exits through the bottom of column 12 into reboiler 38.

However, some of the cumene 36 produced in catalyst bed 18 may be in a vapor state, which can rise upwards into the next stage containing upper glass beads 22. At any given temperature, there is going to be a certain vapor pressure that will indicate the fraction of cumene that will evaporate. In this case, even though the reaction temperature is lower than cumene's boiling point, the vapor pressure of cumene ($P_v$ =34.5 KPa) at the reaction temperature will cause a fraction of the cumene to evaporate. At this temperature, 115° C., benzene vapor pressure is much higher ($P_v$ =265 KPa) than that of cumene, which causes much more benzene to evaporate). Here, the cumene collects on the (cooler) surfaces of glass beads 22, and then falls back down through the catalyst bed 18 and lower glass beads 14, where it exits through the bottom of column 12 into reboiler 38. Hence, by using this design, with a molar excess of benzene inside the reactor, a very high percentage of the propylene gas 28 reacts with benzene to form cumene; while leaving very little un-reacted propylene gas 28 to rise to the top of column 12 and escape through vent pipe 56. Other light gases, such as propane, which may be a contaminant of the propylene feed gas, can also exit through vent pipe 54 (to be burned off, for example).

Excess benzene vapor 40 that exits the top of column 12 enters condenser 46, where it is cooled and condensed back into liquid benzene 32. Then, it flows to is benzene accumulator 48, where it is stored for future use. In one embodiment (i.e., FIG. 1), liquid benzene 32 flows from accumulator 48 to pump 34, and then is re-injected into catalyst bed 18, thereby forming a closed loop where un-reacted benzene is continuously recycled and reused. Make-up liquid benzene 50 is fed from storage tank 52 into accumulator 48 to replace the benzene lost when reacting with propylene to form cumene.

The crude alkylation products 35 (cumene+DIPB), plus any un-reacted liquid benzene 32, leaves the bottom of column 12 and are collected by reboiler 38. Reboiler 38 is heated to at least 80 degrees C (which is the boiling temperature of benzene at room pressure), but less than 152 degrees C (which is the boiling temperature of cumene at room pressure). At these temperatures, reboiler 38 evaporates some of the liquid benzene 32 into benzene vapor 40, which rises back up into reactor column 12, where it can be recycled and reused to make cumene. However, since reboiler 38 is colder than 152 degrees C, the liquid cumene+DIPB 36 pass through reboiler 38 to optional cooler 42, and then finally to receiver 44, where the cumene+DIPB are stored.

Figure 2:
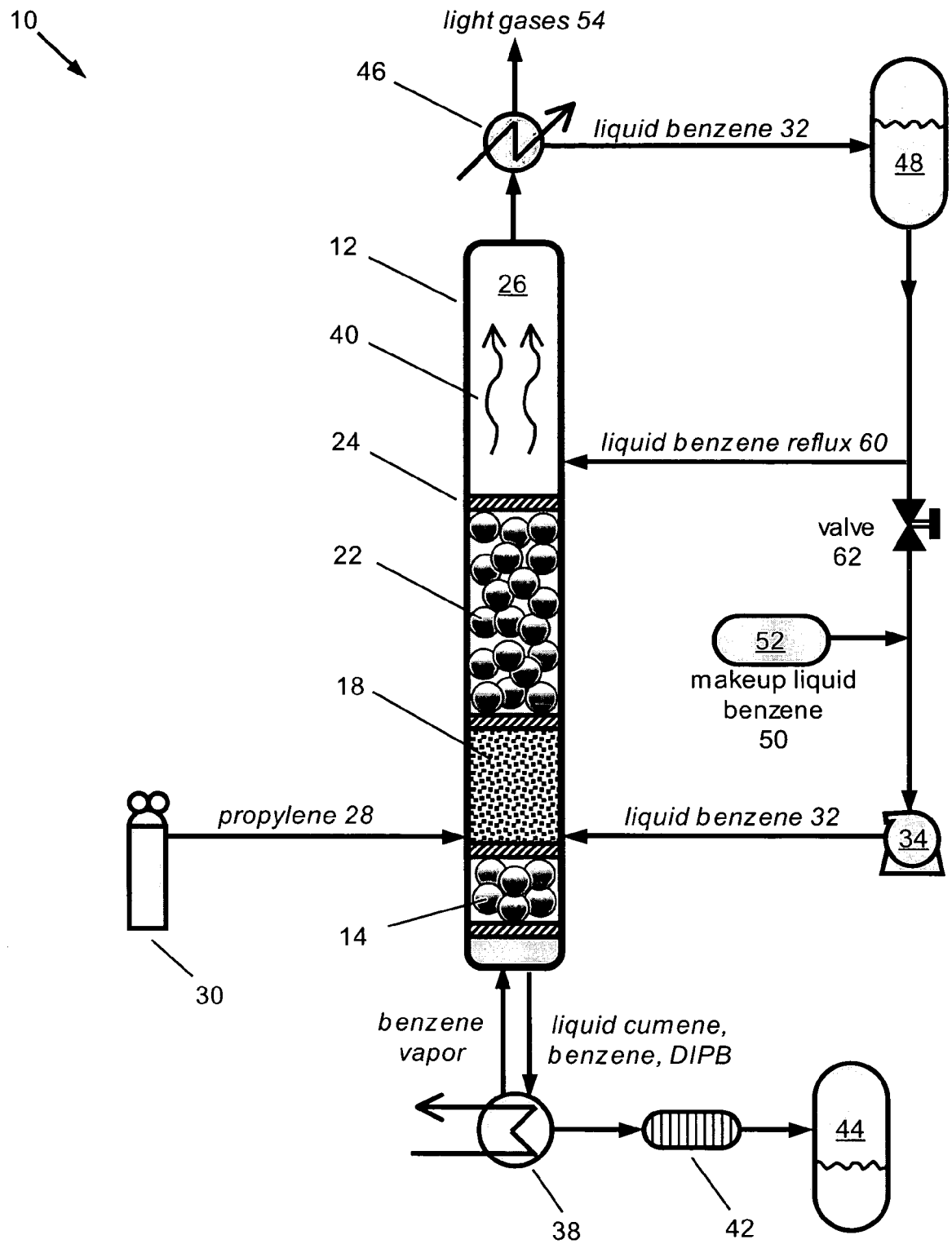
FIG. 2 shows a second example of a schematic process flow chart for producing cumene, including a schematic cross-section view of a reactive separation column, according to the present invention.

FIG. 2 shows a second embodiment of the present invention, where the catalytic reaction separation system 10 additionally comprises means for refluxing benzene back to the upper regions of column 12. Here, some, or all, of the liquid benzene 32 is taken from accumulator 48 and returned (refluxed, recycled) to the upper end of reactor column 12, at some point above catalyst bed 18; where it subsequently falls back down by gravity through open volume 26 and upper glass beads 22 into catalyst bed 18, where it react with propylene gas. Optionally, the benzene reflux stream 60 may be reinjected into the top or the middle of the catalyst bed 18. Control valve 62 can be used to control how much liquid benzene 32 leaving accumulator 48 is refluxed/recycled back to the top of column 12, vs. being recycled via pump 34 into catalyst bed 18. Note that in FIG. 2, the locations for injecting propylene gas 28 and liquid benzene 32 have been moved to the bottom of catalyst bed 18, as an optional position.

Figure 3:
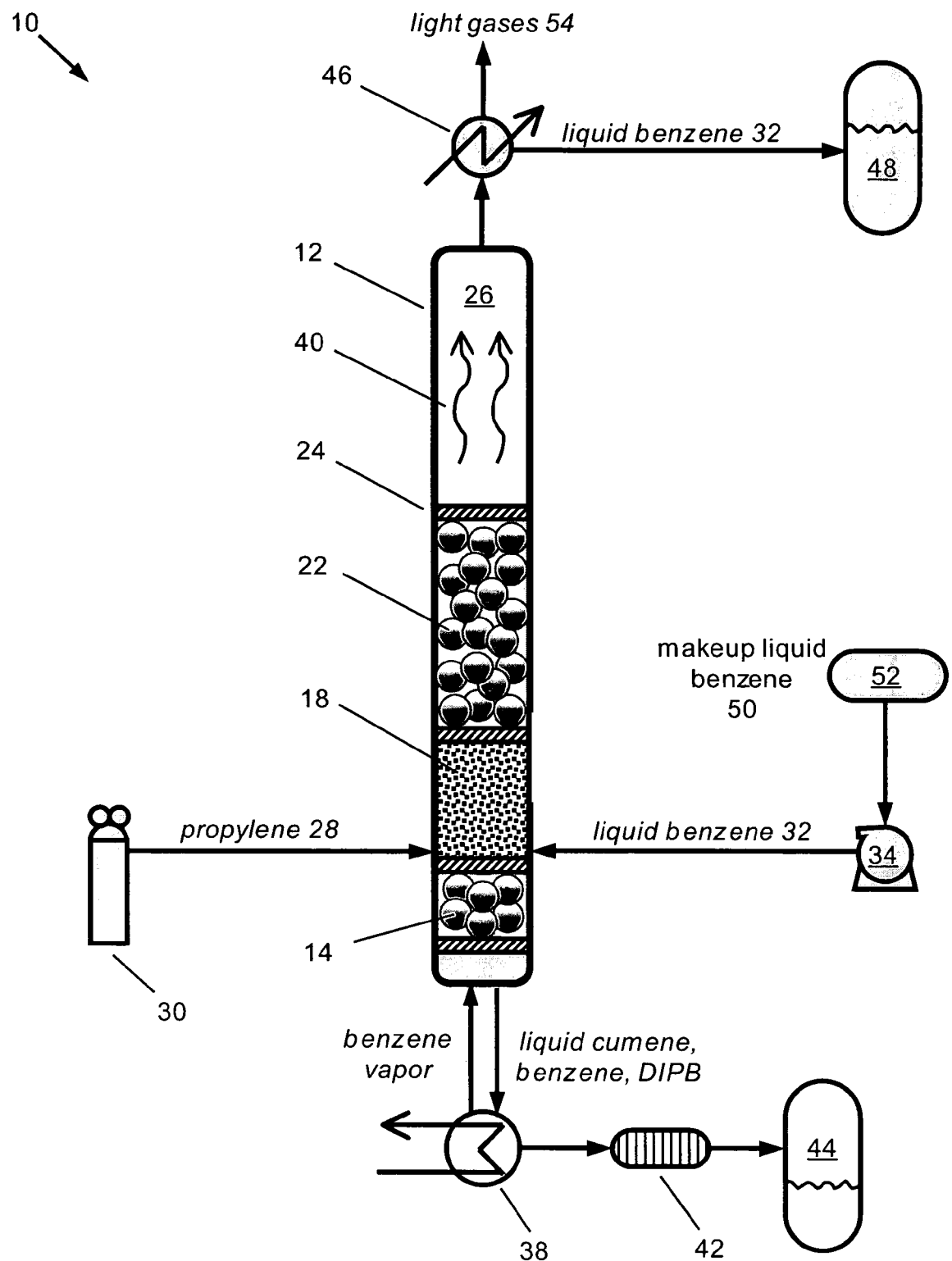
FIG. 3 shows a third example of a schematic process flow chart for producing cumene, including a schematic cross-section view of a reactive separation column, according to the present invention.

FIG. 3 shows a third embodiment of the present invention, wherein all of the un-reacted benzene vapor 40 that has been recovered and liquified by condenser 46 is stored in accumulator 48, with none of it being recycled or refluxed back to reactor column 12.

In all of these embodiments, the reaction (alkylation) temperature of catalyst bed 18 ranges from about 80 degrees C and about 152 degrees C (stated earlier). Alternatively, the catalyst bed temperature can be about 115 degrees C. This range of reaction temperatures is both suitable for producing cumene by reacting propylene with benzene, and is also useful for allowing physical separation of benzene vapor from liquid cumene due to their differences in vapor pressures. The overall system performance (i.e., selectivity, yield, purity, efficiency, etc.) can easily be optimized since the temperature of catalyst bed 18 is independently controllable by adjusting external or internal heating (or cooling) means. For example, at the low end of the range (i.e., 80 degrees C), the vapor pressure of cumene is very low (1.4 psia) compared to benzene (14.7 psia); while at the upper end of the range (e.g., 150 degrees C), where cumene is just starting to boil, the vapor pressure of benzene is quite high (84 psia), compared to that of cumene (14.7 psia).

Examples of catalyst material used in bed 18 may comprise a zeolite-type solid acid catalyst, e.g., protonated (H+)-beta-zeolite in powder form with a $Si/Al_2$ ratio of 25:1. Alternatively, the catalyst may comprise pellets made of a mixture of 80% beta-zeolite (with a $Si:Al_2$ ratio of 24:1) mixed with 20% alumina binder. Beta-zeolites with other $Si:Al_2$ ratios can also be used (e.g., $Si:Al_2$ 300:1-24:1). MCM-22, ZSM-5, and USY catalysts also have good properties for this reaction, and can be used. The zeolites may also be doped with certain active metals to improve their performance. For example, beta zeolite doped with 1 wt % Ga, Pt, La, or Ce, may be used.

The catalyst material (pellets or powders) in catalyst bed 18 are packed tightly and held in place inside of reactor column 12 on top and bottom by lower and upper porous supports 16 and 20, respectively. Porous supports 13, 16, 20, or 24 can be made of quartz wool, glass wool, or a stainless steel wire mesh or porous metal foam.

In one embodiment, the vertical height of catalyst bed 18 may range from about ½ inch to about 2 inches. Preferably, the height is about 1 inch. Such a short height minimizes the amount of pressure drop of liquid or gaseous components flowing through the bed; while, at the same time, producing a significantly large cumene yield and selectivity.

In another embodiment, the vertical height of catalyst bed 18 may be scaled up to greater heights, e.g;, greater than 2 inches. However, as the bed height increases, the pressure drop through the packed catalyst bed also increases; and will eventually limit the practical maximum height of the catalyst bed.

No structured catalysts or structured catalyst particle supports are used in catalyst bed 18. Since the height of bed 18 can be very short (about 1 inch), the pressure drop across the close-packed mass of powders or pellets is not excessive. This short bed height (and reduces column diameter) reduces the cost of the system 10, since expensive structured catalyst elements are not needed.

In another embodiment, where the vertical height of catalyst bed 18 ranges from about ½ inch to about 2 inches, the capacity of the system may be increased in a variety of different ways. In one way, the reactor column 12 may comprise several shallow beds 18 of catalyst particles stacked up vertically in a rack; or separated by a porous support. In another way, the diameter of reactor column 12 may be increased, while keeping the vertical height of catalyst bed 18 short, at about ½ inch to about 2 inches. Since the reactor column 12 is un-pressurized, increasing the column diameter is not so expensive (it's not a pressure vessel). Additionally, to help volatile compounds overcome the pressure drop, a soft vacuum may be used either on the vent on the top, or on the bottom.

Experimental Tests

Figure 4:
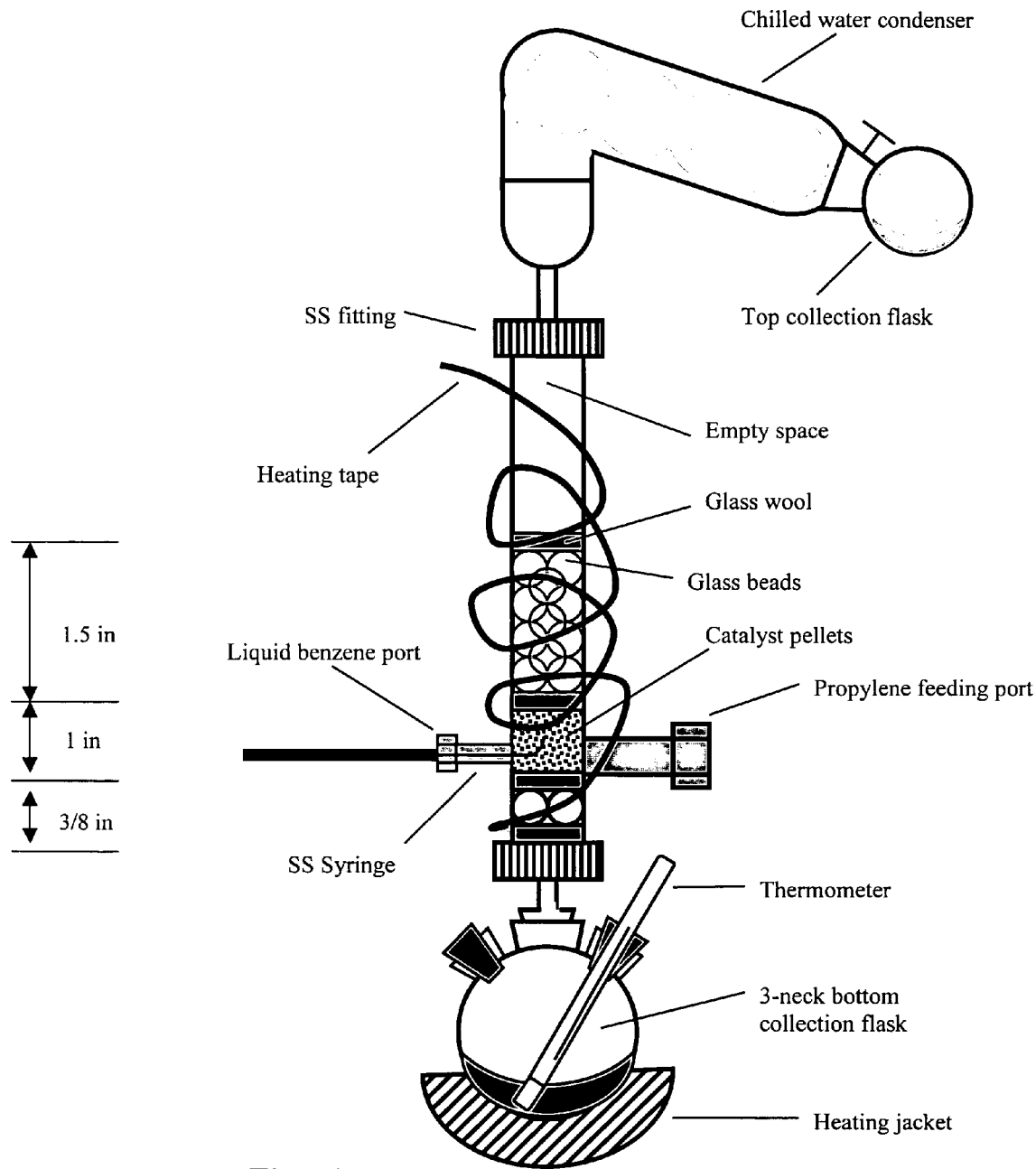
FIG. 4 shows a schematic process flow chart for an experimental laboratory set-up for producing cumene, including a schematic cross-section view of an approximate laboratory-scale reactive separation column, according to the present invention. The reactor size has been exaggerated to show detail.

An experimental reactor was built, as shown schematically in FIG. 4. Two types of catalysts were used: (1) protonated ($H^+$ β) beta-zeolite in powder form ($Si:Al_2$ 25:1); and (2) pellets of 80% Beta-zeolite($Si:Al_2$ 24:1) and 20% alumina binder, purchased from Zeolyst International. Benzene (Aldrich, 99+%) was used without further purification. The alkylating agent, propylene 14.3% in a balance of nitrogen, was purchased premixed from TriGas. Relative cumene yield was defined as the amount of cumene produced over the maximum amount of cumene calculated by stoichiometry. Cumene relative selectivity is the amount of cumene produced over the sum of all the products obtained.

Initial studies were conducted to determine appropriate reaction temperatures and catalyst amounts. Though not fully optimized, 115° C. was chosen as a suitable temperature for these experiments; as it is the intermediate temperature between the boiling points of benzene and cumene (80 degrees C and about 152 degrees C). The choice of 115 degrees C was made as a compromise between the components' relative volatility (which favors choosing a lower temperature, i.e., closer to 80 degrees C, in order to maximize the ability to physically separate benzene vapor from liquid cumene in the column) and the reaction temperature (which favors using a higher temperature, i.e., closer to 152 degrees C to increase the chemical reaction rate). Catalyst amounts of 200 mg for powder, 400 mg for pellets, were chosen not only for the alkylation reaction to occur, but also for the separation of reactants and products.

Figure 5A:
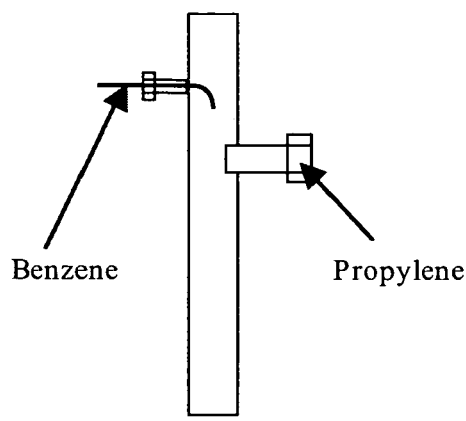
FIGS. 5-A,B,C illustrate three different stainless steel experimental reactor column configurations that were used: (A) six-inch-long column with reactant feeding ports separated by 1 inch, (B) 3.5 inch column with reactant feeding ports separated by 1 inch, and (C) 6 inch column with reactant feeding ports located at the same height.
Figure 5B:
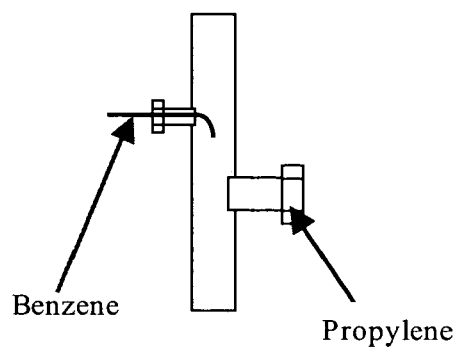

The reactive separation system in FIG. 4 consists of a reactant delivery section, a vertical flow-through catalytic column, and a collection part with a reboiler and condenser. The reactants are fed into the reactor by a mass flow controller that delivers 3.5 ccm of a gaseous mixture of 14.3% of propylene in nitrogen, and a syringe pump that injects 2.7 cc/h of liquid benzene. The system is kept at atmospheric pressure. The reactants were fed through two separate inlets, which could be located at the same level, or at different points, in the vertical column (see configurations A, B, or C in FIGS. 5A, 5B, 5C). The vertical flow-through reactive column consisted of either a 3.5 in. or 6 in. stainless steel tube of ⅜ OD, in which the catalyst was hand-packed and held in place by quartz glass wool and quartz beads. Before beginning the reaction, the catalyst was pretreated by flowing 10 ccm of dry nitrogen through the column at around 115° C. for at least 30 minutes.

Once the column was stable at the reaction temperature of 115° C., the reactants were fed in to start the reaction. A flexible heating tape connected to a heater was wrapped around the reactive column to keep the reactor at the desired temperature.

A chilled-water circulated glass condenser was attached to the top of the column to cool and condense unreacted benzene vapor in a collection glass flask. A reboiler unit, composed of a collection glass bulb and a heating mantle connected to a heating controller, was attached to the bottom of the reactive column to provide heat, and to collect cumene and heavier products. This reboiler unit was kept around 80° C., the boiling point of benzene, in order to evaporate any unreacted liquid benzene and send it back up to the column. After 3 hours of reaction time, the flow of reactants was stopped and the products collected at the top and bottom of the column. The final volume of the collected products of the alkylation reaction was taken to 25 ml using hexane. Then, the products were identified by mass spectroscopy using a GC/MS Hewlett Packard 5890 Series II Plus, and quantitatively analyzed by a Hewlett Packard 5890A gas chromatograph equipped with a capillary column Bentone 34/DNDP SCOT (0.02 in.×50 ft, or 0.5 mm×15.2 m) from Supelco and a flame ionization detector.

We discovered that the reactive separation column, packed with a solid acid catalyst, allowed separation of unreacted excess benzene from the products as they formed. The reactants propylene and benzene met inside the reactive column in the presence of a solid catalyst at 1 atm. and 115° C. As the benzene alkylation reaction proceeded, cumene was formed. At the same time, vapor benzene rose through the column and exited through the top of the tower, together with unreacted propylene, as the light stream; while produced liquid cumene, together with all the other by-products (mainly di-isopropylbenzenes, DIPB), dropped down the column and exited the bottom of the tower as the heavy stream. Ideally, all the unreacted benzene would escape to the top of the column, and all cumene formed would fall with the bottom products.

Table 1 summarizes the results of these experiments. As can be seen, in all the reactor configurations relative cumene selectivity with respect to products was above 85% for both powdered and pelletized catalysts; but the cumene reaction yield, and separation of unreacted benzene and produced cumene varied greatly from one design configuration to another. With configuration A (shown in FIG. 5A), a very low cumene reaction yield occurred, and most of the cumene formed was taken to the bottom, as desired, but most of the unreacted benzene also collected at the bottom. With configuration B (shown in FIG. 5B), the separation of unreacted benzene and produced cumene in the reactor was not very good; similar amounts of reactant and products were obtained in the amounts collected from both the top and bottom.

Figure 5C:
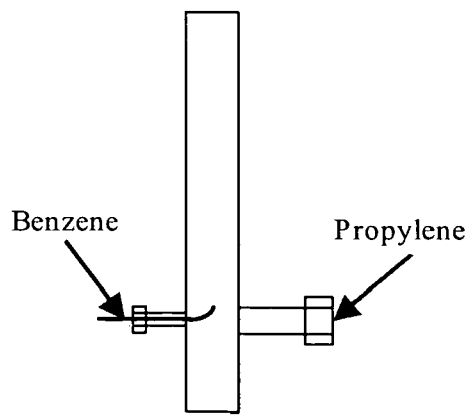

Of the different reactors tested, configuration C shown in FIG. 5C gave the best results in terms of reactant-product separation for both pelletized and powdered catalysts. When pellets were used, 76% of the unreacted benzene rose to the top of the column, but 24% of benzene dropped with the bottom products. With the cumene, 63% dropped to the bottom, but 37% of cumene rose to the top. For this reaction, relative cumene yield was about 30% and cumene selectivity was 90%. When powdered catalyst was used in reactor configuration C, 62% of the unreacted benzene rose to the top of the column, and 86% of the cumene formed in the reaction dropped with the bottom products. The cumene yield for this reaction was about 20% and the relative selectivity was 85%.

As seen, although some of these nonoptimized system configurations do not have the high yield of the reactive distillation processes (above 98%), they do not require the high operating pressures of the other processes; nor do they require the use of a reflux system for the top products. While complete 100% separation of un-reacted benzene from the cumene formed did not generally appear to be possible in one pass, additional testing and design optimization should improve the separation results. The selectivity obtained with our catalytic separation reactions stayed in the 85 percentile at the relatively low reaction temperature of 115° C. and at only 1 atmosphere. To obtain the same selectivity in a conventional batch or fixed-bed reactor system would require a higher reaction temperature (likely above 150° C.). We have not tested the effect that a high benzene:propylene molar ratio, such as the one used in the reactive separation, (22:1) would have in a conventional batch or fixed bed system. The stability of the catalyst with reaction time remains to be studied, as a main drawback of the use of highly active zeolites in cumene production may be their quick deactivation.

In these tests we studied the influence of catalyst morphology and reactant injection port locations. Testing of different reactor configurations for cumene production, using both powdered and pelletized Beta zeolite catalysts, helped in initial optimization of design and production yields. These initial studies showed that this design allowed for selectivity for catalytic separation reactions starting at 85% and above at the relatively low reaction temperature of 115° C. Simultaneously, cumene reaction yield up to 30% was achieved with up to 76% of the unreacted benzene being separated from the products.

The particular examples discussed above are cited to illustrate particular embodiments of the invention. Other applications and embodiments of the apparatus and method of the present invention will become evident to those skilled in the art. It is to be understood that the invention is not limited in its application to the details of construction, materials used, and the arrangements of components set forth in the following description or illustrated in the drawings.

The scope of the invention is defined by the claims appended hereto.

TABLE 1

Results of reactive separation of cumene, with reactor at 115° C. and 1 atm., feeding 3.5 ccm 14.5% propylene/ $N_2$ and 2.7 ml liquid benzene, after 3 hr reaction.

| Run | Catalyst | Reactor configuration | Rel. cumene selectivity, % | Rel. cumene yield, % | wt % benzene top bottom | wt % cumene top bottom |
|---|---|---|---|---|---|---|
| 1 | 200 mg powder | A | 87 | 3 | 31 / 69 | 11 / 89 |
| 2 | 200 mg powder | B | 89 | 21 | 50 / 50 | 62 / 38 |
| 3 | 400 mg pellets | B | 88 | 6 | 51 / 49 | 54 / 46 |
| 4 | 200 mg powder | C | 85 | 20 | 62 / 38 | 14 / 86 |
| 5 | 400 mg pellets | C | 90 | 30 | 76 / 24 | 37 / 63 |

What is claimed is:

1. A catalytic reactive separation system for the production of cumene, comprising:
   a reactive separation column, comprising:
      a packed, solid-acid catalyst bed having a vertical height greater than about ½ inch, and less than about 2 inches, held in place inside of the column by upper and lower porous supports;

a lower zone located below the catalyst bed comprising glass beads;
an upper zone located above the catalyst bed comprising glass beads;
an open volume located above the upper zone of glass beads; and
means for heating or cooling at least part of the column;
first injection means for injecting propylene gas into the catalyst bed from outside the column;
second injection means for injecting liquid benzene into the catalyst bed from outside the column;
means for removing un-reacted liquid benzene, liquid cumene, and other heavy products from the bottom of the column;
benzene condenser means for condensing un-reacted benzene vapor that exits from the top of the column;
benzene accumulator means for accumulating the condensed benzene vapor;
reboiler means for evaporating un-reacted liquid benzene collected from the bottom of the column and returning the evaporated benzene back to the column;
cumene receiver means for storing the liquid cumene and other heavy products that exit from the bottom of the column;
recycle means for recycling un-reacted liquid benzene from the benzene accumulator means back into the reactive separation column the second injection means; and
wherein the first injection means for injecting propylene gas into the catalyst bed and the second injection means for injecting liquid benzene into the catalyst bed are both located at the same vertical height along the column.

2. The catalytic reactive separation system of claim 1, wherein the packed catalyst bed comprises a solid-acid catalyst material selected from the group consisting of powders of protonated (H+ β) beta-zeolite (Si:Al$_2$ 25:1), pellets of 80% β beta-zeolite (Si:Al$_2$ 24:1) mixed with 20% alumina binder, MCM-22 zeolite, ZSM-5 zeolite, and USY catalyst.

3. The catalytic reactive separation system of claim 1, wherein the catalyst bed comprises beta-zeolite doped with about 1 wt% of a metal selected from the group consisting of gallium, platinum, lanthanum, and cerium.

4. The catalytic reactive separation system of claim 1, wherein the reboiler means is heated to a temperature greater than or equal to about 80degrees C, and less than or equal to about 152 degrees C.

5. The catalytic reactive separation system of claim 1, wherein the catalyst bed is heated to a temperature greater than or equal to about 80degrees C, and less than or equal to about 152 degrees C.

6. The catalytic reactive separation system of claim 1, wherein the entire vertical height of the column is heated to a temperature greater than or equal to about 80 degrees C, and less than or equal to about 152 degrees C.

7. The catalytic reactive separation system of claim 1, wherein the catalyst bed is heated to a temperature equal to about 115 degrees C.

8. The catalytic reactive separation system of claim 1, wherein the reactive separation column is operated at atmospheric pressure, and is not constructed as a pressure vessel, and cannot be pressurized above ambient pressure.

9. The catalytic reactive separation system of claim 1, wherein the vertical height of the packed catalyst bed is about 1 inch.

10. The catalytic reactive separation system of claim 1, wherein the packed catalyst bed does not comprise any structured catalyst assemblies.

11. The catalytic reactive separation system of claim 1, further comprising makeup means for supplying makeup liquid benzene to the reactive separation column.

12. The catalytic reactive separation system of claim 1, wherein means for heating or cooling at least part of the column comprises external heating means selected from the group consisting of a electric resistance heating jacket wrapped around the outside of the column, and pipe means for circulating a heated or cooled gas or liquid around the outside of the column.

13. The catalytic reactive separation system of claim 1, wherein the means for heating or cooling at least part of the column comprises internal heating means selected from the group consisting of an internal electric resistance heating element disposed inside of the catalyst bed, and internal pipe means for circulating a heated or cooled gas or liquid inside the catalyst bed.

14. The catalytic reactive separation system of claim 1, wherein the system does not comprise means for pressurizing the reactive separation column above atmospheric pressure.

15. The catalytic reactive separation system of claim 1, wherein the reactive separation column is vented to the ambient environment.

16. The catalytic reactive separation system of claim 1, wherein both the propylene gas and the liquid benzene are injected into the middle of the catalyst bed from outside the column.

17. The catalytic reactive separation system of claim 1, wherein both the propylene gas and the liquid benzene are injected into the bottom of the catalyst bed from outside the column.

18. A method of producing cumene, comprising:
a) providing the catalytic reactive separation system of claim 1;
b) heating the catalyst bed to a temperature greater than or equal to about 80 degrees C, and less than or equal to about 152 degrees C;
c) maintaining the pressure inside the reactive separation column at or below atmospheric pressure;
d) injecting propylene gas into the heated catalyst bed via the first injection means;
e) injecting liquid benzene into the heated catalyst bed via the second injection means;
f) producing cumene by reacting propylene and benzene in the presence of the solid-acid catalyst material;
g) removing un-reacted liquid benzene, liquid cumene, and other heavy products from the bottom of the column;
h) evaporating un-reacted liquid benzene collected from the bottom of the column and returning the evaporated benzene back to the column;
i) condensing un-reacted benzene vapor that exits from the top of the column; and
j) recycling the condensed un-reacted benzene vapor back into the reactive separation Column via the second injection means.

19. The method of producing cumene of claim 18, wherein step j) comprises recycling the condensed un-reacted benzene vapor back into the packed catalyst bed.

* * * * *